US012765946B2

(12) United States Patent
Mauch et al.

(10) Patent No.: US 12,765,946 B2
(45) Date of Patent: Oct. 20, 2026

(54) NEUROMODULATION CATHETER

(71) Applicant: Medtronic Ireland Manufacturing Unlimited Company, Dublin (IE)

(72) Inventors: Kevin Mauch, Windsor, CA (US); William Chang, Santa Rosa, CA (US); Justin Goshgarian, Santa Rosa, CA (US); Sina Som, Santa Rosa, CA (US); Dishuan Chu, Rohnert Park, CA (US); Somashekharayya Hiremath, Rohnert Park, CA (US); Amanda L. Fazekas, San Diego, CA (US); Martha A. Barajas-Torres, Santa Rosa, CA (US)

(73) Assignee: Medtronic Ireland Manufacturing Unlimited Company, Dublin (IE)

(*) Notice: Subject to any disclaimer, the term of this patent is extended or adjusted under 35 U.S.C. 154(b) by 282 days.

(21) Appl. No.: 18/685,447

(22) PCT Filed: Aug. 10, 2022

(86) PCT No.: PCT/EP2022/072406
§ 371 (c)(1),
(2) Date: Feb. 21, 2024

(87) PCT Pub. No.: WO2023/025590
PCT Pub. Date: Mar. 2, 2023

(65) Prior Publication Data

US 2024/0366297 A1 Nov. 7, 2024

Related U.S. Application Data

(60) Provisional application No. 63/236,606, filed on Aug. 24, 2021.

(51) Int. Cl.
*A61B 18/14* (2006.01)
*A61B 18/00* (2006.01)

(52) U.S. Cl.
CPC .................... *A61B 18/1492* (2013.01); *A61B 2018/00434* (2013.01); *A61B 2018/00577* (2013.01);
(Continued)

(58) Field of Classification Search
CPC ...... A61B 18/1492; A61B 2018/00214; A61B 2018/00404; A61B 2018/00434;
(Continued)

(56) References Cited

U.S. PATENT DOCUMENTS 8,888,773 B2 11/2014 Chang et al.
9,717,555 B2 8/2017 Chan et al.
(Continued)

FOREIGN PATENT DOCUMENTS

CN 205433878 U 8/2016
CN 205433879 U 8/2016
(Continued)

OTHER PUBLICATIONS

International Search Report and Written Opinion of International Application No. PCT/EP2022/072406 dated Dec. 15, 2022, 9 pp.
(Continued)

*Primary Examiner* — Khadijeh A Vahdat
(74) *Attorney, Agent, or Firm* — Shumaker & Sieffert, P.A.

(57) ABSTRACT

A catheter may include an elongate body comprising a proximal portion and a distal portion, and a plurality of electrodes carried by the distal portion. The distal portion of the catheter may be configured to transform from a low-profile delivery state to a radially expanded deployed state in which at least some electrodes of 'the plurality of electrodes are deployed at different circumferential positions of the radially expanded deployed slate. A ratio of a deployed electrode length to a diameter of the distal portion of the catheter in the radially expanded deployed state may be less
(Continued)

than or equal to about 2.0. The deployed electrode length is a distance between, in the radially expanded deployed, stole, a proximal-most point of a proximal-most electrode of the plurality of electrodes and a distal-most point of a distal-most electrode of the plurality of electrodes.

20 Claims, 5 Drawing Sheets

(52) U.S. Cl.
CPC ................ *A61B 2018/1467* (2013.01); *A61B 2018/1475* (2013.01)

(58) Field of Classification Search
CPC .. A61B 2018/00577; A61B 2018/1435; A61B 2018/1467; A61B 2018/1475
See application file for complete search history.

(56) References Cited

U.S. PATENT DOCUMENTS

| | | | |
|---|---|---|---|
| 10,166,069 B2 | 1/2019 | Tran et al. | |
| 2012/0116382 A1 | 5/2012 | Ku et al. | |
| 2016/0302857 A1 | 10/2016 | Rothman et al. | |
| 2019/0223949 A1 * | 7/2019 | Coates | A61N 1/0529 |

FOREIGN PATENT DOCUMENTS

| | | |
|---|---|---|
| WO | 2006041881 A2 | 4/2006 |
| WO | 2015191938 A1 | 12/2015 |

OTHER PUBLICATIONS

Terumo, “Iberis—Renal denervation system”, 3 pp., Retrieved from the Internet on Feb. 3, 2016 from URL: http://www.terum••europe.com/en•emea/interventional•cardiology/renal•denervation•system/iberis%C2%AE•renal•denervatio••system#itemspecifications.
Fort Wayne Metals, “HHS Tube”, Downloaded fromhttps://fwmetals.com/what-we-do/products/hhs-tube on, Apr. 7, 2026, 11 pp.

* cited by examiner

NEUROMODULATION CATHETER

This application is a U.S. National Stage entry under 35 U.S.C. § 371 of International Application No. PCT/EP2022/072406, filed Aug. 10, 2022, which claims priority from and the benefit of U.S. Provisional Patent Application No. 63/236,606, filed on Aug. 24, 2021, the entire content of each of which is incorporated herein by reference.

TECHNICAL FIELD

The present technology is related to neuromodulation catheters. In particular, various examples of the present technology are related to neuromodulation catheters for delivering radiofrequency neuromodulation.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function can be considerably stimulated in disease states characterized by heightened sympathetic tone. For example, reduced renal blood flow and glomerular filtration rate as a result of renal sympathetic efferent stimulation may be a cornerstone of the loss of renal function in cardio-renal syndrome (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, can have significant limitations including limited efficacy, compliance issues, side effects, and others.

SUMMARY

The present technology is directed to devices, systems, and methods for neuromodulation, such as renal neuromodulation using radiofrequency (RF) energy. A catheter (e.g., an RF ablation catheter) may be configured to deliver RF energy circumferentially around an anatomical lumen (e.g., a renal main artery, accessory renal artery, or branch vessel) in which the catheter is positioned. The catheter may include at least a proximal portion and a distal portion. The distal portion may include a plurality of electrodes (e.g., at least two electrodes, three electrodes, four electrodes, or the like). The distal portion of the catheter may be configured to transform between a substantially straight delivery configuration and a spiral or helical deployed configuration. In the deployed configuration, the position of the electrodes along the distal portion and the spacing between adjacent turns of the spiral or helix may be selected so that a length between a proximal-most electrode and a distal-most electrode is relatively small. This may result in RF energy delivery in a substantially continuous toroid shape. By delivering RF energy in such a manner, a substantially continuous circumferential lesion may be formed in tissue, which may reduce a likelihood of renal nerves being left untreated improve a likelihood of success of the denervation therapy.

In some examples, the disclosure describes a catheter that includes an elongate body comprising a proximal portion and a distal portion, and a plurality of electrodes carried by the distal portion. The distal portion of the catheter may be configured to transform from a low-profile delivery state to a radially expanded deployed state in which at least some electrodes of the plurality of electrodes are deployed at different circumferential positions of the radially expanded deployed state. A ratio of a deployed electrode length to a diameter of the distal portion of the catheter in the radially expanded deployed state may be less than or equal to about 2.0. The deployed electrode length is a distance between, in the radially expanded deployed state, a proximal-most point of a proximal-most electrode of the plurality of electrodes and a distal-most point of a distal-most electrode of the plurality of electrodes.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout and wherein.

DETAILED DESCRIPTION

Figure 1:
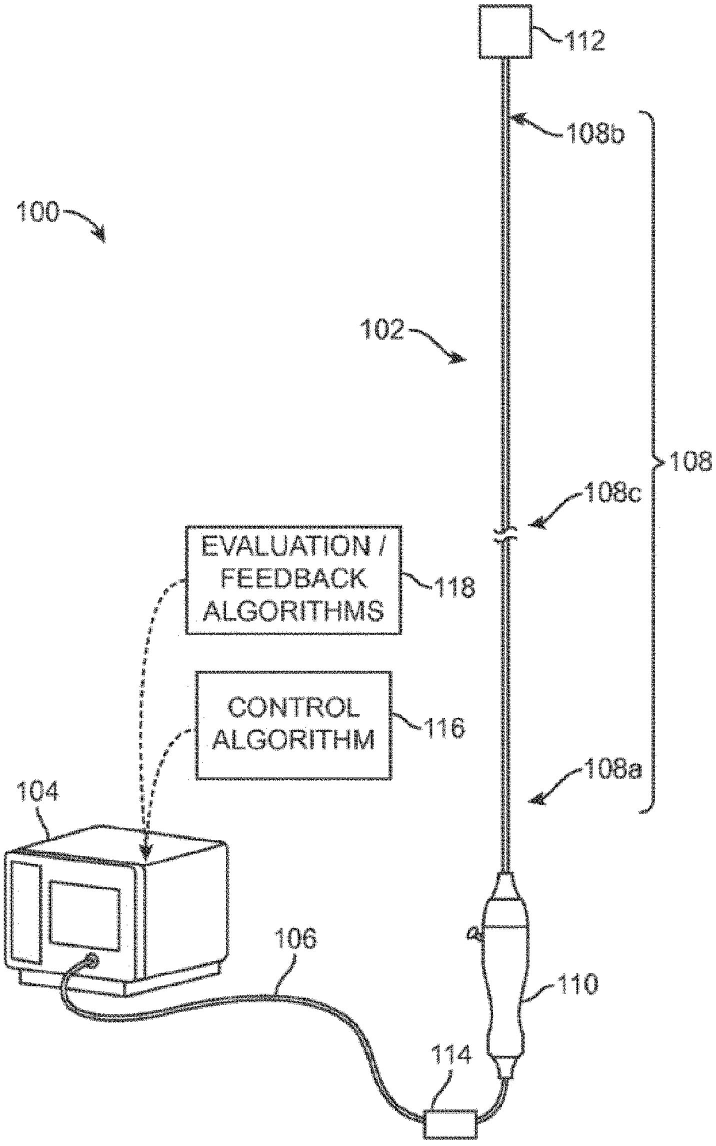
FIG. 1 is a partially schematic illustration of a neuromodulation system configured in accordance with some examples of the present disclosure.

The present technology is directed to devices, systems, and methods for neuromodulation, such as renal neuromodulation, using radiofrequency (RF) energy.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

Renal neuromodulation, such as renal denervation, may be used to modulate activity of one or more renal nerves and may be used to affect activity of the sympathetic nervous system (SNS). In renal neuromodulation, one or more therapeutic elements may be introduced near renal nerves located between an aorta and a kidney of a patient. In some examples, the one or more therapeutic elements may be carried by or attached to a catheter, and the catheter may be introduced intravascularly, e.g., into a renal artery via a brachial artery, femoral artery, or radial artery approach. In other examples, the one or more therapeutic elements may be introduced extravascularly, e.g., using a laparoscopic technique.

Renal neuromodulation can be accomplished using one or more of a variety of treatment modalities, including electrical stimulation, radio frequency (RF) energy, microwave energy, ultrasound energy, a chemical agent, or the like. In some examples, an RF ablation system includes an RF generator configured to generate RF energy and deliver RF energy to tissue via one or more electrodes carried by a catheter and positioned within an anatomical lumen of a body of a patient. For example, the anatomical lumen may be a vessel, such as a vein or artery. In some examples, the anatomical lumen may be a renal artery, such as a main renal artery, an accessory renal artery, a branch vessel, or the like. The RF energy may heat tissue to which the RF energy is directed (which tissue includes one or more renal nerves) and modulate the activity of the one or more renal nerves.

The RF ablation system may be configured to deliver RF energy via either a monopolar or bipolar arrangement. In a monopolar arrangement, a return or reference electrode may be paced on a patient's skin, and one or more of the electrodes carried by the catheter may be driven to act as active electrodes, either simultaneously or sequentially. In a bipolar arrangement, the active and return electrodes may both be carried by or attached to the catheter and introduced within the body of the patient. In some examples, a catheter includes a plurality of electrodes, and the RF generator and electrical connections between the RF generator and the electrodes can be configured for monopolar RF energy delivery, bipolar RF energy delivery, or can be controllable between monopolar RF energy delivery and bipolar RF energy delivery.

In many patients, renal nerves generally follow the renal artery and branch vessels from near the aorta to a kidney. The renal nerves may be present in a wall of the renal artery and/or branch vessels and/or in tissue surrounding the renal artery and/or branch vessels. Because renal nerves may be around the renal artery and/or branch vessels and may include multiple nerves and/or nerve branches, it may be desirable to deliver RF energy circumferentially around the renal artery and/or branch vessels to affect as many renal nerves as possible.

In accordance with examples of the current disclosure, a catheter (e.g., an RF ablation catheter) is configured to deliver RF energy circumferentially around an anatomical lumen (e.g., a renal main artery, accessory renal artery, or branch vessel) in which the catheter is positioned. The catheter includes at least a proximal portion and a distal portion. The distal portion may include a plurality of electrodes (e.g., at least two electrodes, three electrodes, four electrodes, or the like) and may be configured to transform between a substantially straight delivery configuration and a spiral or helical deployed configuration. In the deployed configuration, the position of the electrodes along the distal portion and the spacing between adjacent turns of the spiral or helix may be selected so that a length between a proximal-most electrode and a distal-most electrode is relatively small. This may result in RF energy delivery in a substantially continuous toroid shape. By delivering RF energy in such a manner, a substantially continuous circumferential lesion (e.g., a ring-like lesion formed by a plurality of lesions overlapping in a circumferential plane) may be formed in tissue, which may reduce a likelihood of renal nerves being left untreated and improve a likelihood of success of the denervation therapy.

FIG. 1 is a partially schematic perspective view illustrating a therapeutic system 100 configured in accordance with some examples of the present disclosure. Therapeutic system 100 includes a neuromodulation catheter 102, an RF generator 104, and a cable 106 extending between catheter 102 and RF generator 104. Neuromodulation catheter 102 includes an elongate shaft (also referred to as an elongate body) 108 having a proximal portion 108*a*, a distal portion 108*b*, and an optional intermediate portion 108*c* between proximal portion 108*a* and distal portion 108*b*. Neuromodulation catheter 102 may further include a handle 110 operably connected to shaft 108 via proximal portion 108*a* and a neuromodulation element 112 (shown schematically in FIG. 1 that is part of or attached to distal portion 108*b*. Shaft 108 is configured to locate the neuromodulation element 112 at a treatment location within or otherwise proximate to an anatomical lumen (e.g., a blood vessel, a duct, an airway, or another naturally occurring anatomical lumen within the human body). In some examples, shaft 108 is configured to locate neuromodulation element 112 at an intraluminal (e.g., intravascular) location. Neuromodulation element 112 may be configured to provide or support a neuromodulation treatment at the treatment location. Shaft 108 and neuromodulation element 112 may measure 2, 3, 4, 5, 6, or 7 French or other suitable sizes.

Intraluminal delivery of neuromodulation catheter 102 may include percutaneously inserting a guidewire (not shown) into an anatomical lumen of a patient and moving shaft 108 and neuromodulation element 112 along the guide wire until neuromodulation element 112 reaches a suitable treatment location. Alternatively, neuromodulation catheter 102 may be a steerable or non-steerable device configured for use without a guidewire. Additionally, or alternatively, neuromodulation catheter 102 may be configured for use with another type of guide member, such as a guide catheter or a sheath (not shown), alone, or in addition to a guidewire.

RF generator 104 is configured to control, monitor, supply, and/or otherwise support operation of neuromodulation catheter 102. In other examples, neuromodulation catheter 102 may be self-contained or otherwise configured for operation independent of RF generator 104. When present, RF generator 104 is configured to generate a selected form and/or magnitude of RF energy for delivery to tissue at a treatment location via neuromodulation element 112. For example, RF generator 104 can be configured to generate RF energy (e.g., monopolar and/or bipolar RF energy). In other examples, RF generator 104 may be another type of device configured to generate and deliver another suitable type of energy to neuromodulation element 112 for delivery to tissue at a treatment location via electrodes (not shown) of neuromodulation element 112.

Along cable 106 or at another suitable location within therapeutic system 100, therapeutic system 100 may include a control device 114 configured to initiate, terminate, and/or adjust operation of one or more components of neuromodulation catheter 102 directly and/or via RF generator 104. RF generator 104 may be configured to execute an automated control algorithm 116 and/or to receive control instructions from an operator. Similarly, in some implementations, RF generator 104 is configured to provide feedback to an operator before, during, and/or after a treatment procedure via an evaluation/feedback algorithm 118.

Figure 2:
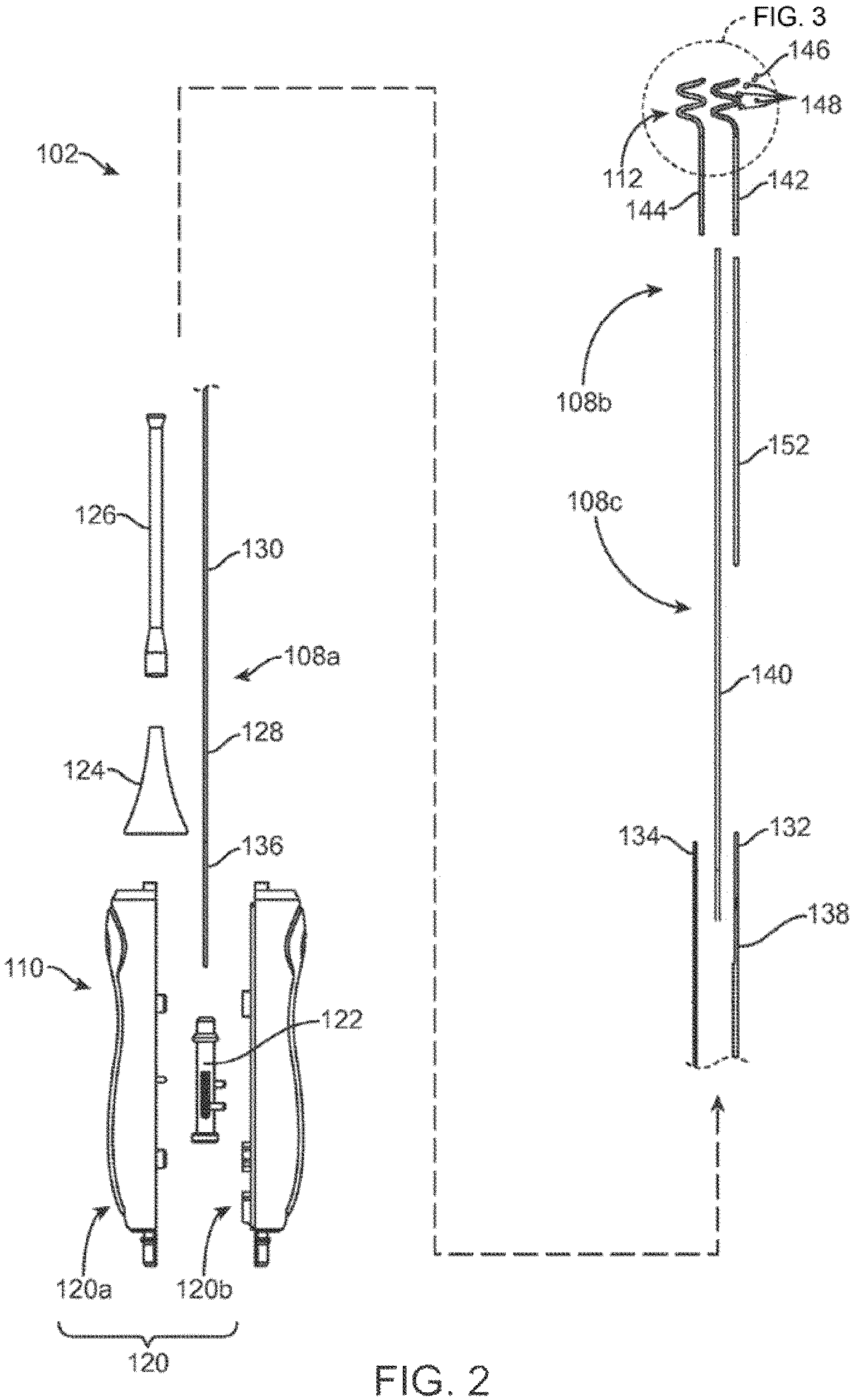
FIG. 2 is an exploded profile view of the catheter shown in FIG. 1.
Figure 3:
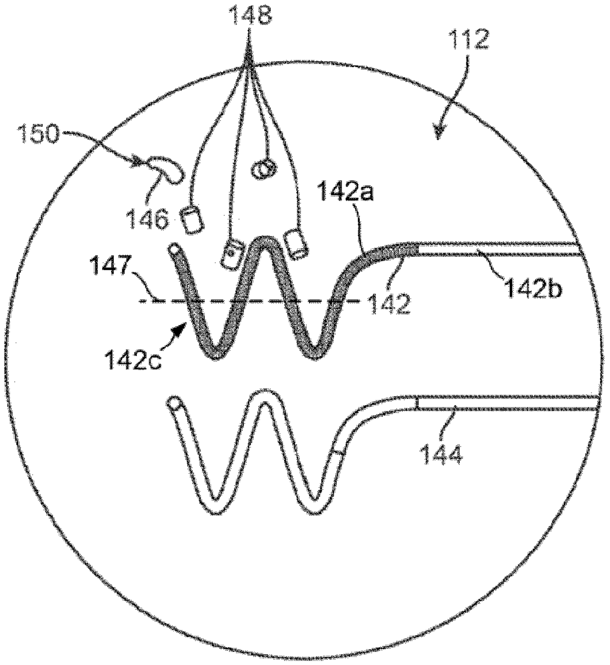
FIG. 3 is an enlarged exploded profile view of a portion of the catheter shown in FIG. 1 taken at the location designated in FIG. 2.

FIG. 2 is an exploded profile view of an example of neuromodulation catheter 102. FIG. 3 is an enlarged exploded profile view of a distal portion of the example of neuromodulation catheter 102 taken at the location designated in FIG. 2. In some examples, as shown with reference to FIGS. 2 and 3 together, handle 110 includes mating shell segments 120 (individually identified as shell segments 120*a* and 120*b*) and a connector 122 (e.g., a luer connector) operably positioned between mating shell segments 120. Handle 110 may further include a distally tapered strain-relief element 124 operably connected to distal ends of the shell segments 120. In some examples, slidably positioned over shaft 108, catheter 102 includes a loading tool 126 configured to facilitate loading catheter 102 onto a guidewire (not shown). When assembled, shaft 108 can extend through coaxial lumens (also not shown) of strain-relief element 124 and loading tool 126 (if present), respectively, and between shell segments 120 to connector 122.

Shaft 108 may include an assembly of tubular segments. At proximal portion 108*a* and extending distally though at least a portion of intermediate portion 108*c*, shaft 108 can include a proximal hypotube segment 128, a proximal jacket 130, a first electrically insulative tube 132, and, optionally, a guidewire tube 134. In some implementations, first electrically insulative tube 132 and guidewire tube 134 are disposed side-by-side within proximal hypotube segment 128. First electrically insulative tube 132 can be configured to carry electrical leads (not shown) and to electrically insulate the electrical leads from the proximal hypotube segment 128. Guidewire tube 134 is configured to receive a guide wire (not shown). Proximal jacket 130 may be disposed around at least a portion of an outer surface of the proximal hypotube segment 128. Proximal hypotube segment 128 may include a proximal stem 136 at its proximal end and a distal skive 138 at its distal end.

In some examples, rather than guidewire tube 134 extending within proximal portion 108*a*, guidewire tube 134 may not extend within proximal portion 108*a*, but may exit near a junction of proximal portion 108*a* and intermediate portion 108*c* (e.g., catheter 102 may be a rapid exchange catheter).

First electrically insulative tube 132 and guidewire tube 134 (if present in proximal portion 108*a*) extend distally beyond distal skive 138 of proximal end portion 108*a*. Shaft 108 may, in some examples, include intermediate tube 140 beginning proximally at a region of shaft 108 at which the first electrically insulative tube 132 and guidewire tube 134 (if present in proximal portion 108*a*) distally emerge from proximal hypotube segment 128. Intermediate tube 140 may be more flexible than proximal hypotube segment 128. At the region of shaft 108 at which first electrically insulative tube 132 and guidewire tube 134 (if present) distally emerge from proximal hypotube segment 128, intermediate tube 140 may be coaxially aligned with proximal hypotube segment 128 so as to receive first electrically insulative tube 132 and guidewire tube 134 (if present). From this region, intermediate tube 140 extends distally to distal portion 108*b* of shaft 108. In some examples, first electrically insulative tube 132 distally terminates within intermediate tube 140. In contrast, guidewire tube 134 extends through the length of intermediate tube 140 to distal portion 108*b*. At a distal end of intermediate tube 140, intermediate tube 140 can be operably connected to distal portion 108*b*, which includes or carries neuromodulation element 112.

Distal portion 108*b* may include a shape memory structure 142 coupled to the distal end of intermediate tube 140. Distal portion 108*b* also may include a distal jacket 144 disposed around at least a portion of an outer surface of shape memory structure 142. As shown, distal portion 108*b* includes a neuromodulation element 112 that includes electrodes 148 carried by or attached to distal jacket 144 at spaced-apart positions along a longitudinal axis of distal jacket 144 (shown in exploded view in FIG. 3). In some examples, electrodes 148 may include band electrodes. At a distal end of shape memory structure 142, neuromodulation element 112 may include a distally tapering atraumatic tip 146, which may include a distal opening 150 configured to allow a guidewire (not shown) to pass through the opening 150. The electrical leads can respectively extend through the distal jacket 144 (e.g., between an inner surface of distal jacket 144 and an outer surface of shape memory structure 142) to band electrodes 148.

A distal portion or end of guidewire tube 134 may connect to a proximal portion or end of shape memory structure 142 or may extend within a lumen defined by shape memory structure 142.

In FIGS. 2 and 3, distal portion 108*b* and neuromodulation element 112 are shown in a radially expanded deployed state, although FIGS. 2 and 3 are not to scale. Distal portion 108*b* and neuromodulation element 112 may be configured to transition between a low-profile delivery state to the radially expanded deployed state shown in FIGS. 2 and 3. When distal portion 108*b* and neuromodulation element 112 are in the radially expanded deployed state, shape memory structure 142 can have a shape that is more helical (spiral) than its shape when neuromodulation element 112 is in the low-profile delivery state. In other words, shape memory structure 142 may be configured to urge distal portion 108*b* toward the helical shape. In at least some examples, shape memory structure 142 has the more helical shape when at rest and is configured to be forced into the less helical shape by an external sheath (not shown) or an internal guidewire (not shown). For example, shape memory structure 142 may be urged to the less helical shape (e.g., the low-profile delivery state) by introducing the guidewire through guidewire tube 134 and the lumen defined by shape memory structure 142. Neuromodulation catheter 102 may be advanced through an anatomical lumen (e.g., vessels of a patient) to position distal portion 108*b* and neuromodulation element 112 at a treatment site. The guidewire then may be retracted proximally from at least distal portion 108*b* and neuromodulation element 112 to allow shape memory structure 142 to recover toward or to the more helical shape and transition distal portion 108*b* and neuromodulation element to a more helical shape.

In some examples, shape memory structure 142 may be formed to define a shape in which a transition region 142*a* from the straight portion 142*b* to a helical portion 142*c* is shaped to maintain tangency between straight portion 142*b* and helical portion 142*c*. In other words, as seen in the side view of FIG. 3, the straight portion 142*b* of shape memory structure 142 sits at approximately the same radial distance from a central axis 147 of helical portion 142*c* as the coils of helical portion 142*c*. Alternatively, or additionally, transition region 142*a* may include a curve that transitions from straight portion 142*b* to helical portion 142*c* gradually and along an arc of a circle traced by helical portion 142*c* when viewing an end view of shape memory structure 142. In this way, shape memory structure 142 may omit any transverse sections (e.g., sections that are transverse to central axis 174 of helical portion 142*c*). This may facilitate advancing the guidewire through the lumen of shape memory structure 142 when shape memory structure is in the more helical shape (e.g., in the radially expanded deployed state).

Shape memory structure 142 may be made of a shape memory material, such as nitinol. In some examples, shape memory structure 142 includes a multi-filar tube including a plurality of filars that are formed from shape memory material. For example, shape memory structure 142 may be a helical hollow strand, such as HHSR tube available from Fort Wayne Metals Research Products Corp., Fort Wayne, Indiana. As an example, shape memory structure 142 may be a helical hollow strand tube with 9 or 11 nitinol strands and an inner diameter of about 0.018 inch (about 457 micrometers) and an outer diameter of about 0.025 inch (about 635 micrometers).

In some examples, the material of shape memory structure 142 is electrically conductive. Accordingly, neuromodulation element 112 may include a second electrically insulative tube 152 disposed around an outer surface of the shape memory structure 142 so as to electrically separate band electrodes 148 from shape memory structure 142. In some examples, first and second electrically insulative tubes 132, 152 are made at least partially (e.g., predominantly or entirely) of polyimide, polyethylene terephthalate (PET), polyether block amide (e.g., PEBAX®), or combinations thereof. In other examples, first and second electrically insulative tubes 132, 152 may be made of other suitable electrically insulative materials.

In some examples, instead of or in addition to using the combination of a guidewire and shape memory structure 142 to transition distal portion 108*b* from the low-profile delivery state to the radially expanded deployed state, other actuating mechanisms may be used. For example, a pull wire may be attached near the distal tip of distal portion 108*b* and axial forces may be used to transition distal portion 108*b* from the low-profile delivery state to the radially expanded deployed state (e.g., a proximally directed axial force on the pull wire may transition distal portion 108*b* from the low-profile delivery state to the radially expanded deployed state, and a relaxation of the proximally directed axial force on the pull wire may transition distal portion 108*b* from the radially expanded deployed state to the low-profile delivery state). As another example, a push member may be attached near the distal tip of distal portion 108*b* and axial forces may be used to transition distal portion 108*b* from the low-profile delivery state to the radially expanded deployed state (e.g., a proximally directed axial force on the push member may transition distal portion 108*b* from the low-profile delivery state to the radially expanded deployed state, and a distally directed axial force on the push member may transition distal portion 108*b* from the radially expanded deployed state to the low-profile delivery state).

In accordance with techniques of this disclosure, distal portion 108*b* is configured to assume a relatively longitudinally compact shape when in the radially expanded deployed state. For instance, spacing between adjacent turns of distal portion 108*b* when in the radially expanded deployed state may be relatively small (e.g., less than about 10 millimeters (mm)). This may enable positioning of electrodes 148 in a nearly circular configuration when distal portion 108*b* in the radially expanded deployed state. In turn, this positioning of electrodes 148 may allow formation of substantially continuous circumferential lesion in adjacent tissue (e.g., a blood vessel wall or tissue adjacent to a blood vessel wall) upon delivery of RF energy by electrodes 148. This may reduce a likelihood of renal nerves being left untreated improve a likelihood of success of the denervation therapy and improve a clinical outcome of renal denervation therapy.

Figure 4:
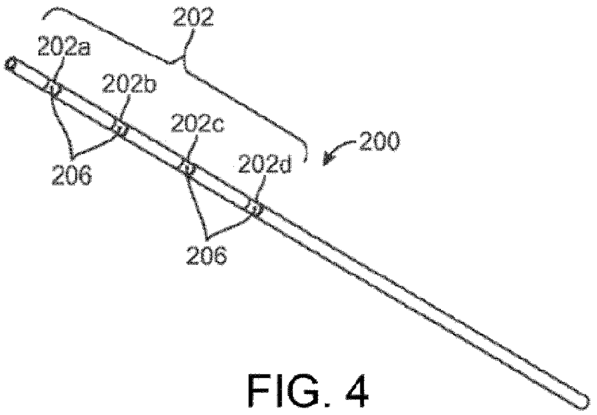
FIG. 4 is a perspective view of a distal jacket of a neuromodulation element of a neuromodulation catheter configured in accordance with examples of the present disclosure.
Figure 5:
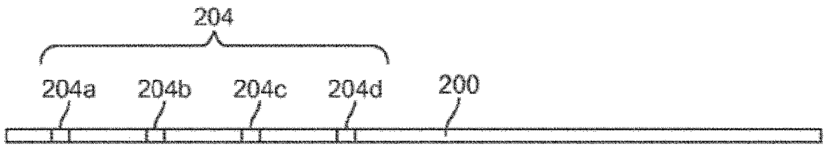
FIG. 5 is a profile view of the distal jacket shown in FIG. 4 and band electrodes seated straight in the reduced-diameter segments, in accordance with some examples of the present disclosure.
Figure 6:
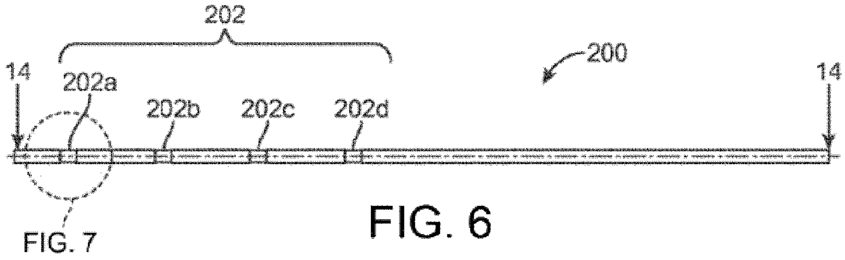
FIG. 6 is a profile view of the distal jacket shown in FIG. 10.
Figure 7:
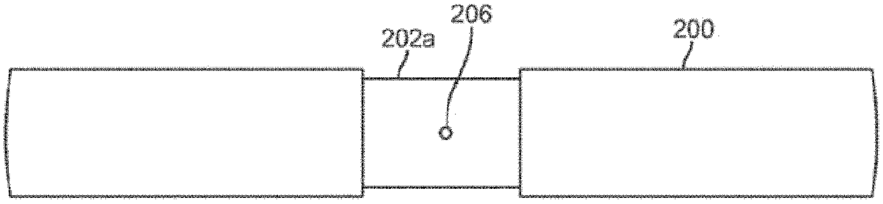
FIG. 7 is an enlarged profile view of a portion of the distal jacket shown in FIG. 4 taken at a location designated in FIG. 6.

FIG. 4 is a perspective view of a distal jacket 200 of a neuromodulation element of a neuromodulation catheter configured in accordance with some examples of the present disclosure. Distal jacket 200, for example, can be used in neuromodulation element 112 (FIGS. 1-3) in place of distal jacket 144 (FIGS. 2 and 3). Accordingly, distal jacket 200 be described below in conjunction with components of catheter 102 (FIGS. 1 and 2). Distal jacket 200 may include reduced-diameter segments 202 (individually identified as reduced-diameter segments 202*a*-202*d*) extending into its outer surface. FIG. 5 is a profile view of the distal jacket 200 and band electrodes 204 (individually identified as band electrodes 204*a*-204*d*) respectively seated straight in the reduced-diameter segments 202. FIG. 6 is a profile view of the distal jacket 200 without the band electrodes 204. FIG. 7 is an enlarged profile view of a portion of the distal jacket 200 taken at a location designated in FIG. 6.

With reference to FIGS. 4-7 together, distal jacket 200 may be substantially tubular (e.g., tubular or nearly tubular to the extent permitted by manufacturing tolerances) and configured to be disposed around at least a portion of an outer surface of shape memory structure 142 (FIGS. 2 and 3). Generally, distal jacket 200 may include a plurality of reduced-diameter segments 202. Reduced-diameter segments 202 may be insets, pockets, grooves, or other suitable structural features configured to respectively position or seat the band electrodes 204. In some examples, reduced-diameter segments 202 extend around an entire circumference of distal jacket 200. In the illustrated example, distal jacket 200 includes four reduced-diameter segments 202 spaced apart along a longitudinal axis of distal jacket 200. Alternatively, the distal jacket 200 can include one, two, three, five, six or a greater number of reduced-diameter segments 202. Reduced-diameter segments 202 may be spaced apart at equal distances or at different distances. For example, the reduced-diameter segments 202 are equally spaced such that an equal distance is present between each adjacent pair of adjacent reduced-diameter segments 202. Once band electrodes 204 are respectively seated in the reduced diameter segments 202, outer surfaces of band electrodes 204 and distal jacket 200 between reduced diameter segments 202 can be at least generally flush. This can be useful for example to reduced or eliminate potentially problematic ridges (e.g., circumferential steps) at distal and proximal ends of individual band electrodes 204. Distal jacket 200 may include a plurality of openings 206, one opening positioned at each reduced-diameter segment 202. A neuromodulation catheter including distal jacket 200 may include electrical leads (not shown) extending from respective reduced-diameter segments 202, through respective openings 206, through a lumen of the outer jacket 144 (FIGS. 2 and 3), through intermediate tube 140, and through proximal hypotube segment 128 to handle 110. In this way, the electrical leads can respectfully electrically connect band electrodes 204 to proximal components of a neuromodulation catheter including distal jacket 200.

Figure 8:
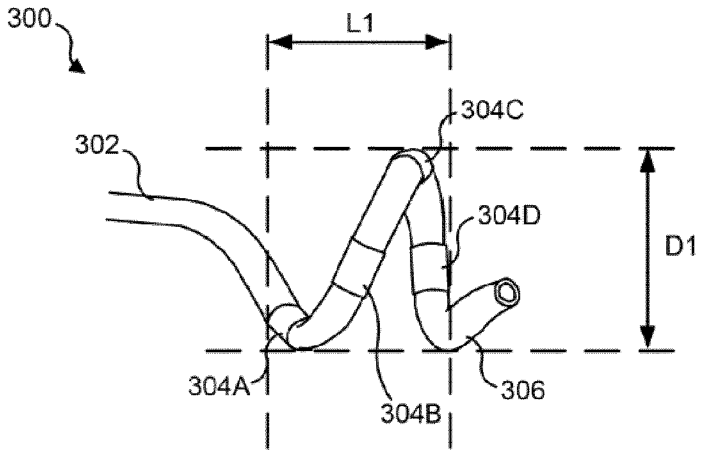
FIG. 8 is a side view of an example distal portion of an example neuromodulation catheter in a radially expanded deployed state.

In some examples, the shape of distal portion 108*b* of catheter 102 (FIGS. 1-3) when in the radially expanded deployed state may be characterized by a deployed electrode length, a deployed electrode length ratio, or both. FIG. 8 is a side view of an example distal portion 302 of an example neuromodulation catheter 300 in a radially expanded deployed state.

Neuromodulation catheter 300 is an example of catheter 102.

In the example shown in FIG. 8, distal portion 302 includes a plurality of electrodes 304A-304D (collectively, "electrodes 304") carried by an outer jacket 306, which is an example of distal jackets 144, 200. Although not shown in FIG. 8, distal portion 302 also may include a shape memory structure, which may be similar to or substantially the same as shape memory structure 142.

Distal portion 302 includes any suitable number of electrodes 304. For example, distal portion 302 may include at least two electrodes, at least three electrodes, at least four electrodes, exactly three electrodes, exactly four electrodes, or the like. The number of electrodes may be selected based on one or more of a variety of factors, including, for example, a number of channels provided by RF generator 104 (FIG. 1), desired flexibility of distal portion 302, desired continuity (e.g., circumferential continuity) or shape of the RF energy field delivered by electrodes 304, or the like. For example, more electrodes 304 may tend to improve continuity (e.g., circumferential continuity) or shape of the RF energy field while generally reducing flexibility of distal portion 302 and/or conformability of distal portion 302 to a wall of the anatomical lumen in which catheter 300 is disposed. Conversely, fewer electrodes 304 or electrodes of shorter length may tend to reduce continuity (e.g., circumferential continuity) or shape of the RF energy field while generally increasing flexibility of distal portion 302 and/or conformability of distal portion 302 to a wall of the anatomical lumen in which catheter 300 is disposed.

In some examples, each electrode of electrodes 304 may be disposed within distal portion 302 at a position along outer jacket 306 that deploys into a helical or spiral shape, as shown in FIG. 8. In other examples, one or more of electrodes 304 may be disposed within distal portion 302 at a position along outer jacket 306 that does not deploy into a helical or spiral shape, e.g., that remains in a substantially straight configuration upon deployment of distal portion 302. For example, in other implementations, proximal-most electrode 304A, distal electrode-most 304D, or both may be within distal portion 302 at a position along outer jacket 306 that does not deploy into a helical or spiral shape. In some instances, an electrode of electrodes 304 that is at a position along outer jacket 306 that does not deploy into a helical or spiral shape may not be used to deliver energy during the therapy delivered using neuromodulation catheter 300. For example, neuromodulation catheter 300 may include three electrodes (e.g., the three more distal electrodes) at positions along outer jacket 306 that deploy into a helical or spiral shape and one electrode (e.g., the proximal-most electrode) at a position along outer jacket 306 that does not deploy into a helical or spiral shape.

The size of electrodes 304 also may affect the flexibility, conformability, and/or performance of distal portion 302. For example, longer electrodes 304 (measured parallel to a longitudinal axis of neuromodulation catheter 300) may tend to reduce flexibility of distal portion 302 and/or conformability of a deployed distal portion 302 to a wall of the anatomical lumen in which neuromodulation catheter 300 is disposed. Conversely, shorter electrodes 304 (measured parallel to a longitudinal axis of catheter 300) may tend to increase flexibility of distal portion 302 and/or conformability of distal portion 302 to a wall of the anatomical lumen in which neuromodulation catheter 300 is disposed. Reduced conformability may result in a larger minimum diameter for distal portion 302 in the radially expanded deployed state, reduced contact between electrodes 304 and a wall of the anatomical lumen in which neuromodulation catheter 300 is deployed, or the like. In some examples, one or more electrodes 304 may have a length, measured parallel to a longitudinal axis of neuromodulation catheter 300, of less than about 2.0 mm, such as about 1.5 mm, or less than about 1.5 mm, or about 1 mm, or less than about 1 mm.

The diameter of electrodes 304 also may affect the flexibility and performance of distal portion 302. For example, larger diameter electrodes 304 may tend to increase a length between a proximal-most point of proximal electrode 304A and a distal-most point of distal electrode 304D when catheter 300 is in the radially expanded deployed state. Conversely, smaller diameter electrodes may tend to decrease a length between a proximal-most point of proximal electrode 304A and a distal-most point of distal electrode 304D when catheter 300 is in the radially expanded deployed state. In some examples, electrodes 304 may have a diameter between about 0.5 mm and about 1.5 mm, such as about 1 mm. In each of these examples as well as other examples described herein, "about" may refer to +/−10% or +/−5% of the recited value.

The physical construction of electrodes 304 also may affect the flexibility and performance of distal portion 302. For example, ring electrodes formed of a relatively rigid material may tend to decrease flexibility of distal portion 302, while ring electrodes formed of a relatively flexible material, or printed electrodes, or vapor deposited electrodes, or coiled electrodes, may tend to increase flexibility of distal portion 302.

Electrodes 304 may be spaced along distal portion 302 of catheter 300 with any desired spacing. The spacing between adjacent electrodes 304 may be measured from a point on one electrode (e.g., a proximal end, a distal end, or a longitudinal center of the electrode) to the same point on an adjacent electrode (e.g., a proximal end, a distal end, or a longitudinal center of the adjacent electrode). The spacing between adjacent electrodes 304 may affect a positioning of electrodes 304 circumferentially about helical or spiral shape (and, thus, the wall of the anatomical lumen in which neuromodulation catheter 300 is deployed). As such, the spacing between adjacent electrodes 304 may be selected based on a deployed diameter of distal portion 302 or a range of deployed diameters of distal portion 302. For example, the spacing between adjacent electrodes 304 may be selected to achieve substantially equal distribution of electrodes 304 about a circumference of the anatomical lumen (e.g., vessel) in which distal portion 302 of neuromodulation catheter 300 is deployed.

In some examples, spacing between adjacent electrodes 304 may be between about 1 mm and about 6 mm, such as between about 2 mm and about 4 mm, or between about 2 mm and about 3.5 mm, or about 2 mm, or about 2.5 mm, or about 3 mm, or about 3.5 mm. As examples, for a distal portion 302 having a deployed diameter of about 5 mm, the spacing between adjacent electrodes 304 may be about 2 mm; for a distal portion 302 having a deployed diameter of about 5.5 mm, the spacing between adjacent electrodes 304 may be about 2.5 mm; for a distal portion 302 having a deployed diameter of about 6.5 mm, the spacing between adjacent electrodes 304 may be about 3 mm; and for a distal portion 302 having a deployed diameter of about 8 mm, the spacing between adjacent electrodes 304 may be about 3.5 mm. Other values for the spacing between adjacent electrodes 304 are possible and within the scope of this disclosure.

Electrodes 304 may be formed from any suitable electrically conductive material. The electrically conductive material may be biocompatible. For example, electrodes 304 may include gold, platinum/iridium, or the like.

The structure of distal portion 302 and electrodes 304 may be characterized by a deployed electrode length and/or a deployed electrode length ratio. As used herein, a deployed electrode length means a distance, measured along a longitudinal axis of neuromodulation catheter 300 when distal portion is in the radially expanded deployed state, between a proximal-most point of the proximal-most electrode used to deliver neuromodulation energy (e.g., proximal electrode 304A) and a distal-most point of the distal-most electrode used to deliver neuromodulation energy (e.g., distal electrode 304D). In examples in which one or more electrodes are not used to deliver neuromodulation energy, as explained above, the one or more electrodes not used to deliver neuromodulation energy are not included when determining the deployed electrode length and the deployed electrode length ratio. The deployed electrode length is labelled L1 in FIG. 8.

As used herein, a deployed electrode length ratio refers to a ratio of a deployed electrode length to a diameter (e.g., an outer diameter) of distal portion 302 of catheter 300 in a radially expanded deployed state. When neuromodulation catheter 300 is positioned in an anatomical lumen (e.g., a blood vessel such as a renal artery), the diameter of distal portion 302 of neuromodulation catheter 300 in the radially expanded deployed state may generally be constrained to the inner diameter of the anatomical lumen, which may affect the deployed electrode length and the deployed electrode length ratio. As such, the deployed electrode length and the deployed electrode length ratio may be a function of the inner diameter of the anatomical lumen in which distal portion 302 of neuromodulation catheter 300 is positioned.

A smaller deployed electrode length ratio indicates a more longitudinally compressed deployment of electrodes 304, and, thus, a more circular arrangement of electrodes when distal portion 302 of neuromodulation catheter 300 is in the radially expanded deployed state. Conversely, a larger deployed electrode length ratio indicates a less longitudinally compressed deployment of electrodes 304, and, thus, a more elongated helical arrangement of electrodes when neuromodulation catheter 300 is in the radially expanded deployed state. In FIG. 8, the deployed electrode length ratio is L1/D1, where D1 is the diameter of distal portion 302 of neuromodulation catheter 300 in the radially expanded deployed state.

In some examples, neuromodulation catheter 300 defines a deployed electrode length, L1, of between about 1 mm and about 15 mm, such as between about 1 mm and about 10 mm, or about 1 mm and about 7 mm, or between about 1 mm and about 6 mm, or between about 4 mm and about 7 mm.

In some examples, neuromodulation catheter 300 defines a deployed electrode length ratio of less than 2, such as less than 1.8, or less than 1.5, or less than 1.2, or less than 1.0 or less than 0.9, or less than 0.8. In some examples, neuromodulation catheter 300 may define a deployed electrode length ratio of greater than 0.1, such as greater than 0.2, or greater than 0.3. For example, neuromodulation catheter 300 may define a deployed electrode length ratio of less than about 2.0 for an anatomical lumen having a diameter of between about 3 mm and about 8 mm. As another example, neuromodulation catheter 300 may define a deployed electrode length ratio of less than about 1.5 for an anatomical lumen having a diameter of between about 4 mm and about 8 mm. As another example, neuromodulation catheter 300 may define a deployed electrode length ratio of less than about 1.2 for an anatomical lumen having a diameter of between about 5 mm and about 8 mm. As another example, neuromodulation catheter 300 may define a deployed electrode length ratio of less than about 1.0 for an anatomical lumen having a diameter of between about 6 mm and about 8 mm. As another example, neuromodulation catheter 300 may define a deployed electrode length ratio of less than about 0.9 for an anatomical lumen having a diameter of between about 7 mm and about 8 mm. As another example, neuromodulation catheter 300 may define a deployed electrode length ratio of less than about 0.8 for an anatomical lumen having a diameter of about 8 mm.

Distal portion 302 of neuromodulation catheter 300 may be formed using a variety of techniques. For example, a shape memory structure of distal portion 302 (e.g., shape memory structure 142 shown in FIGS. 2 and 3) may be heat set to have a desired radially deployed expanded state, including diameter, number of turns, spacing between adjacent turns, and deployed length. A mandrel, pre-formed wire, or the like may be used to form the shape memory structure to the desired shape during the heat set. Electrodes 304 and outer jacket 306 may be coupled to the shape memory structure using any suitable technique. For example, outer jacket 306 may include a pre-formed polymer tube that is placed over and around the shape memory structure. Holes may be formed in outer jacket 306 to allow wires connected to electrodes 304 to extend through distal jacket 306, into a lumen of outer jacket 306 (e.g., between outer jacket 306 and the shape memory structure). The wires may be threaded through distal portion 302 to a proximal end of distal portion 302. The distal portion 302 then may be attached to the remainder of catheter, such as an intermediate portion or a proximal portion of neuromodulation 300.

Distal portion 302 of neuromodulation catheter 300 may thus exhibit a longitudinally compressed deployed electrode length compared to some other neuromodulation catheters. This may enable neuromodulation catheter 300 to provide a more focused, ring-like (or circular or toroidal) ablation pattern due to the positioning of electrodes 304. This ablation pattern may be favorable for forming a circumferential lesion, which may provide a similar level of denervation from a single application of RF energy compared to multiple ablations using a neuromodulation catheter with a longer deployed electrode length. This may reduce the procedure time. In some examples, this may allow a single ablation to be performed at the distal main renal artery (for each kidney), where renal nerves are expected to be closer to the artery, while achieving a similar level of denervation compared to multiple ablations using a neuromodulation catheter with a longer deployed electrode length.

Figure 9:
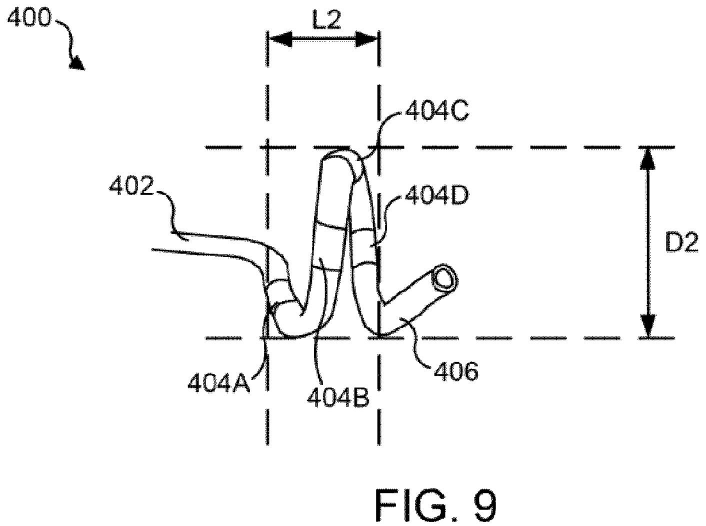
FIG. 9 is a side view of an example distal portion of an example neuromodulation catheter in a radially expanded deployed state.

In some examples, a distal portion of a catheter may be configured to exhibit a more circular (e.g., as opposed to helical or spiral) shape in the radially expanded deployed state. For instance, the shape memory structure may be formed to have a more circular shape, with little or substantially no space between adjacent turns of the shape memory structure. FIG. 9 is a side view of an example distal portion 402 of an example neuromodulation catheter 400 in a radially expanded deployed state. Neuromodulation catheter 400 is another example of catheter 102.

Like neuromodulation catheter 300 of FIG. 8, neuromodulation catheter 400 includes a distal portion 402 that includes a plurality of electrodes 404A-404D (collectively, "electrodes 404") and a distal jacket 406. In the radially expanded deployed state, distal portion 402 exhibits a more circular shape (e.g., a substantially circular shape, such that all electrodes 404 lie within a longitudinal length (measured parallel to a length of the anatomical lumen or vessel in which neuromodulation catheter 400 is deployed) that is three diameters of an electrode or electrodes 404 or less). That is, L2, the distance between a proximal-most point of proximal-most electrode 404A and a distal-most point of distal-most electrode 404B may be less than or equal to about 3 times a diameter of one of electrodes 404. In some examples, the distance between a proximal-most point of proximal-most electrode 404A and a distal-most point of distal-most electrode 404B may be less than or equal to about 2 times a diameter of one of electrodes 404 or may be substantially equal to a diameter of one of electrodes 404.

In some examples, distal portion 402 exhibits a substantially continuous, smooth curve when transitioning from the substantially straight proximal part of distal portion 402 and the more circular shape of the radially expanded deployed part of distal portion 402. For instance, in the radially expanded deployed state, distal portion 402 may not include any portions oriented along a radius or diameter of the circle defined by distal portion 402. This may facilitate re-insertion of the guidewire (not shown) through the lumen defined by distal portion 402 (e.g., defined by the shape memory structure within distal portion 402) to transition distal portion 402 from the radially expanded deployed state to the low-profile delivery state (e.g., a substantially straight configuration). In contrast, if distal portion 402 included relatively sharp turns at the transition between the substantially straight proximal part of distal portion 402 and the more circular shape of the radially expanded deployed part of distal portion 402, the guidewire may be more likely to puncture distal portion 402 while being reinserted, leading to potential difficulty in returning distal portion 402 to the low-profile delivery state.

Catheters configured in accordance with at least some embodiments of the present technology can be well suited (e.g., with respect to sizing, flexibility, operational characteristics, and/or other attributes) for performing renal neuromodulation in human patients. Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, or induced in another suitable manner or combination of manners at one or more suitable treatment locations during a treatment procedure. The treatment location can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include an electrode-based treatment modality alone or in combination with another treatment modality. Electrode-based treatment can include delivering electricity and/or another form of energy to tissue at or near a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity.

Heating effects of electrode-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° Celsius (C)) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of luminal structures that perfuse the target neural fibers. In cases where luminal structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of luminal structures that perfuse the target fibers. In some patients, it can be desirable to heat tissue to temperatures that are sufficient to ablate the target neural fibers or the luminal structures, but that are less than about 90° C. (e.g., less than about 85° C., less than about 80° C., or less than about 75° C.).

The above detailed descriptions of examples of the technology are not intended to be exhaustive or to limit the technology to the precise form disclosed above. Although specific examples of the technology are described above for illustrative purposes, various equivalent modifications are possible within the scope of the technology, as those skilled in the relevant art will recognize. For example, while steps are presented in a given order, alternative examples may perform steps in a different order. The various examples described herein may also be combined to provide further examples. All references cited herein are incorporated by reference as if fully set forth herein. Each embodiment and each aspect so defined may be combined with any other embodiment or with any other aspect unless clearly indicated to the contrary.

From the foregoing, it will be appreciated that specific examples of the present disclosure have been described herein for purposes of illustration, but that various modifications may be made without deviating from the present disclosure. For example, while particular features of the neuromodulation catheters were described as being part of a single device, in other examples, these features can be included on one or more separate devices that can be positioned adjacent to and/or used in tandem with the neuromodulation catheters to perform similar functions to those described herein.

Certain aspects of the present disclosure described in the context of particular examples may be combined or eliminated in other examples. Further, while advantages associated with certain examples have been described in the context of those examples, other examples may also exhibit such advantages, and not all examples need necessarily exhibit such advantages to fall within the scope of the present disclosure. Accordingly, the present disclosure and associated technology can encompass other examples not expressly shown or described herein.

Further, although techniques have been described in which a neuromodulation catheter is positioned at a single location within a single renal artery, in other examples, the neuromodulation catheter may be repositioned to a second treatment site within the single renal artery (e.g., proximal or distal of the first treatment site, may be repositioned in a branch of the single artery, may be repositioned within a different renal vessel on the same side of the patient (e.g., a renal vessel associated with the same kidney of the patient), may be repositioned in a renal vessel on the other side of the patient (e.g., a renal vessel associated with the other kidney of the patient), or any combination thereof. At each location where the neuromodulation catheter is positioned, renal neuromodulation may be performed using any of the techniques described herein or any other suitable renal neuromodulation technique, or any combination thereof.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "about" or "approximately," when preceding a value, should be interpreted to mean plus or minus 10% of the value, unless otherwise indicated. Additionally, the term "comprising" is used throughout to mean including at least the recited feature(s) such that any greater number of the same feature and/or additional types of other features are not precluded.

Aspects and embodiments of the invention may be defined by the following clauses.

Clause 1. A catheter comprising:

an elongate body comprising a proximal portion and a distal portion; and a plurality of electrodes carried by the distal portion, wherein the distal portion of the catheter is configured to transform from a low-profile delivery state to a radially expanded deployed state in which at least some electrodes of the plurality of electrodes are deployed at different circumferential positions of the radially expanded deployed state, wherein a ratio of a deployed electrode length to a diameter of the distal portion of the catheter in the radially expanded deployed state is less than or equal to about 2.0, and wherein the deployed electrode length is a distance between, in the radially expanded deployed state, a proximal-most point of a proximal-most electrode of the plurality of electrodes and a distal-most point of a distal-most electrode of the plurality of electrodes.

Clause 2. The catheter of clause 1, wherein the outer diameter of the distal portion of the catheter is configured to be constrained by a vessel in which the distal portion of the catheter is positioned, and wherein the ratio of the deployed electrode length to the diameter of the distal portion of the catheter in the radially expanded deployed state is less than or equal to about 2.0 for a vessel having a diameter of between about 3 mm and about 8 mm.

Clause 3. The catheter of clause 1 or 2, wherein the outer diameter of the distal portion of the catheter is configured to be constrained by a vessel in which the distal portion of the catheter is positioned, and wherein the ratio of the deployed electrode length to the diameter of the distal portion of the catheter in the radially expanded deployed state is less than or equal to about 1.5 for a vessel having a diameter of between about 4 mm and about 8 mm.

Clause 4. The catheter of any one of clauses 1 to 3, wherein the outer diameter of the distal portion of the catheter is configured to be constrained by a vessel in which the distal portion of the catheter is positioned, and wherein the ratio of the deployed electrode length to the diameter of the distal portion of the catheter in the radially expanded deployed state is less than or equal to about 1.2 for a vessel having a diameter of between about 5 mm and about 8 mm.

Clause 5. The catheter of any one of clauses 1 to 4, wherein the outer diameter of the distal portion of the catheter is configured to be constrained by a vessel in which the distal portion of the catheter is positioned, and wherein the ratio of the deployed electrode length to the diameter of the distal portion of the catheter in the radially expanded deployed state is less than or equal to about 1.0 for a vessel having a diameter of between about 6 mm and about 8 mm.

Clause 6. The catheter of any one of clauses 1 to 5, wherein the outer diameter of the distal portion of the catheter is configured to be constrained by a vessel in which the distal portion of the catheter is positioned, and wherein the ratio of the deployed electrode length to the diameter of the distal portion of the catheter in the radially expanded deployed state is less than or equal to about 0.9 for a vessel having a diameter of between about 7 mm and about 8 mm.

Clause 7. The catheter of any one of clauses 1 to 6, wherein the outer diameter of the distal portion of the catheter is configured to be constrained by a vessel in which the distal portion of the catheter is positioned, and wherein the ratio of the deployed electrode length to the diameter of the distal portion of the catheter in the radially expanded deployed state is less than or equal to about 0.8 for a vessel having a diameter of about 8 mm.

Clause 8. The catheter of any one of clauses 1 to 7, wherein the deployed electrode length is less than or equal to about 6 mm.

Clause 9. The catheter of any one of clauses 1 to 8, wherein, when the elongate body is in the low-profile delivery state, a spacing between electrodes of the plurality of electrodes is less than or equal to 6 mm.

Clause 10. The catheter of any one of clauses 1 to 8, wherein, when the elongate body is in the low-profile delivery state, a spacing between electrodes of the plurality of electrodes is about 2 mm to about 4 mm.

Clause 11. The catheter of any one of clauses 1 to 10, wherein the outer diameter of the distal portion of the catheter is configured to be constrained by an anatomical lumen, and wherein, in the radially expanded deployed state, electrodes of the plurality of electrodes are substantially evenly positioned about an inner circumference of the vessel.

Clause 12. The catheter of any one of clauses 1 to 11, wherein the plurality of electrodes comprises at least three electrodes.

Clause 13. The catheter of any one of clauses 1 to 12, wherein the catheter includes exactly three electrodes.

Clause 14. The catheter of any one of clauses 1 to 12, wherein the catheter includes exactly four electrodes.

Clause 15. The catheter of any one of clauses 1 to 14, wherein a diameter of an electrode of the plurality of electrodes is about 1 mm.

Clause 16. The catheter of any one of clauses 1 to 15, wherein a diameter of each electrode of the plurality of electrodes is about 1 mm.

Clause 17. The catheter of any one of clauses 1 to 16, wherein a length of an electrode of the plurality of electrodes is less than or equal to about 1.5 mm, the length being measured along a longitudinal axis of the elongate body.

Clause 18. The catheter of any one of clauses 1 to 17, wherein a length of each electrode of the plurality of electrodes is less than or equal to about 1.5 mm, the length being measured along a longitudinal axis of the elongate body.

Clause 19. The catheter of any one of clauses 1 to 17, wherein a length of an electrode of the plurality of electrodes is about 1 mm, the length being measured along a longitudinal axis of the elongate body.

Clause 20. The catheter of any one of clauses 1 to 19, wherein the distal portion further comprises a shape memory structure, and wherein the shape memory structure is pre-formed to urge the distal portion toward the radially expanded deployed state.

Clause 21. The catheter of clause 20, wherein the shape memory structure comprises a helical hollow strand.

Clause 22. The catheter of any one of clauses 1 to 21, wherein, in the radially expanded deployed state, the plurality of electrodes are configured to cause a circumferentially continuous lesion to form in tissue surrounding a vessel in which the distal portion is deployed upon delivery of RF energy using the plurality of electrodes.

Clause 23. The catheter of any one of clauses 1 to 22, wherein the distal portion is configured to be positioned in a renal vessel having a diameter of less than or equal to 8 mm.

What is claimed is:

1. A catheter comprising:

an elongate body comprising:

a multi-filar tube comprising a plurality of filars, the multi-filar tube defining an inner diameter of 457 micrometers or less and an outer diameter of 635 micrometers or greater, and a proximal portion and a distal portion; and a plurality of electrodes carried by the distal portion, wherein:

the distal portion of the elongate body is configured to transform from a low-profile delivery state to a radially expanded deployed state in which at least some electrodes of the plurality of electrodes are deployed at different circumferential positions of the radially expanded deployed state, a ratio of a deployed electrode length to a diameter of the distal portion of the elongate body in the radially expanded deployed state is less than or equal to 2.0, the deployed electrode length is a distance between, in the radially expanded deployed state, a proximal-most point of a proximal-most electrode of the plurality of electrodes and a distal-most point of a distal-most electrode of the plurality of electrodes, the distal portion of the elongate body is defined by a portion of the elongate body from the proximal-most point of the proximal-most electrode of the plurality of electrodes to the distal-most point of the distal-most electrode of the plurality of electrodes, wherein the diameter of the distal portion is configured to be constrained by a vessel in which the distal portion is positioned, the vessel having a diameter of between 3 mm and 8 mm, and the plurality of electrodes are configured to deliver radio frequency (RF) energy in a substantially continuous toroid shape.

2. The catheter of claim 1, wherein the ratio of the deployed electrode length to the diameter of the distal portion in the radially expanded deployed state is less than or equal to 2.0.

3. The catheter of claim 1, wherein the ratio of the deployed electrode length to the diameter of the distal portion in the radially expanded deployed state is less than or equal to 1.5, wherein the diameter is between 4 mm and 8 mm.

4. The catheter of claim 1, wherein the ratio of the deployed electrode length to the diameter of the distal portion in the radially expanded deployed state is less than or equal to 1.2, wherein the diameter is between 5 mm and 8 mm.

5. The catheter of claim 1, wherein the ratio of the deployed electrode length to the diameter of the distal portion in the radially expanded deployed state is less than or equal to 1.0, wherein the diameter is between 6 mm and 8 mm.

6. The catheter of claim 1, wherein the ratio of the deployed electrode length to the diameter of the distal portion in the radially expanded deployed state is less than or equal to 0.9, wherein the diameter is between 7 mm and 8 mm.

7. The catheter of claim 1, wherein the ratio of the deployed electrode length to the diameter of the distal portion in the radially expanded deployed state is less than or equal to 0.8, wherein the diameter is 8 mm.

8. The catheter of claim 1, wherein the deployed electrode length is less than or equal to 6 mm.

9. The catheter of claim 1, wherein, when the elongate body is in the low-profile delivery state, a spacing between electrodes of the plurality of electrodes is less than or equal to 6 mm.

10. The catheter of claim 1, wherein the diameter of the distal portion is configured to be constrained by an anatomical lumen, and wherein, in the radially expanded deployed state, electrodes of the plurality of electrodes are substantially evenly positioned an inner circumference of the anatomical lumen.

11. The catheter of claim 1, wherein the plurality of electrodes comprises at least three electrodes.

12. The catheter of claim 1, wherein the catheter includes exactly three electrodes.

13. The catheter of claim 1, wherein a diameter of an electrode of the plurality of electrodes is 1 mm.

14. The catheter of claim 1, wherein a diameter of each electrode of the plurality of electrodes is 1 mm.

15. The catheter of claim 1, wherein a length of an electrode of the plurality of electrodes is less than or equal to 1.5 mm, the length being measured along a longitudinal axis of the elongate body.

16. The catheter of claim 1, wherein a length of each electrode of the plurality of electrodes is less than or equal to 1.5 mm, the length being measured along a longitudinal axis of the elongate body; or wherein a length of an electrode of the plurality of electrodes is 1 mm, the length being measured along a longitudinal axis of the elongate body.

17. The catheter of claim 1, wherein the distal portion further comprises a shape memory structure, and wherein the shape memory structure is pre-formed to urge the distal portion toward the radially expanded deployed state.

18. The catheter of claim 1, wherein, in the radially expanded deployed state, the plurality of electrodes are configured to cause a circumferentially continuous lesion to form in tissue surrounding a vessel in which the distal portion is deployed upon delivery of radiofrequency (RF) energy using the plurality of electrodes.

19. The catheter of claim 1, wherein, when the elongate body is in the low-profile delivery state, a spacing between electrodes of the plurality of electrodes is 2 mm to 4 mm.

20. The catheter of claim 1, wherein the catheter has only four electrodes.

* * * * *